US008121372B2

(12) United States Patent
Härer et al.

(10) Patent No.: US 8,121,372 B2
(45) Date of Patent: Feb. 21, 2012

(54) METHOD FOR REDUCING IMAGE NOISE IN THE CONTEXT OF CAPTURING AN IMAGE USING TWO DIFFERENT RADIATION SPECTRA

(75) Inventors: Wolfgang Härer, Erlangen (DE); Dr. Klaus Klingenbeck-Regn, Nürnberg (DE); Ernst-Peter Rührnschopf, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 788 days.

(21) Appl. No.: 12/229,755

(22) Filed: Aug. 26, 2008

(65) Prior Publication Data
US 2009/0060313 A1    Mar. 5, 2009

(30) Foreign Application Priority Data
Aug. 28, 2007 (DE) .......................... 10 2007 040 519

(51) Int. Cl.
*G01K 9/00* (2006.01)
(52) U.S. Cl. ......................................... 382/130; 378/62
(58) Field of Classification Search ............... 378/62, 378/98.12, 5, 51, 54, 98.9; 382/128, 130
See application file for complete search history.

(56) References Cited

U.S. PATENT DOCUMENTS

| | | | |
|---|---|---|---|
| 4,792,900 A | 12/1988 | Sones et al. | |
| 5,115,394 A | 5/1992 | Walters | |
| 7,010,092 B2 | 3/2006 | Winsor | |
| 2009/0147919 A1 * | 6/2009 | Goto et al. | ...................... 378/86 |

FOREIGN PATENT DOCUMENTS
JP    WO20060123581    * 11/2006

OTHER PUBLICATIONS

Erich Krestal: Editor; "Imaging Systems for Medical Diagnostics"; 1990; pp. 375- 377; ISBN 3-8009-1564-2; Siemens AG, Berlin and Munich, Germany.
R. J. Warp and J.T. Dobbins; "Quantitative evaluation of noise reduction strategies in dual-energy imaging"; Med. Phys. vol. 30, No. 2; Feb. 2003.
W.A. Kalender, E. Klotz and L. Kostaridou; "An Algorithm for noise suppression in Dual Energy CT Material Density Images"; IEEE Trans. Med. Imaging, vol. 7, No. 3; Sep. 1988, pp. 218-224.
C.H. Mc Collough, M.S. Van Lysel, W.W. Peppler and C.A. Mistretta; "A correlated noise reduction algorithm for dual-energy digital subtraction angiography"; Med. Phys. vol. 16, No. 6; Nov./ Dec. 1989; pp. 873-880.

* cited by examiner

*Primary Examiner* — Hoon Song

(57) ABSTRACT

The invention relates to a method for reducing image noise in the context of capturing at least one radiation-based image of a region of interest using two different radiation spectra, in particular two different x-ray radiation spectra, comprising the following steps: capturing raw images of the region of interest using the two different radiation spectra with in each case mutually paired measured values; and to separate different materials in the region of interest, applying to the captured raw images at least one inversion operator with integrated noise filtering, said operator describing a transition from a measured value pair to an assigned reconstruction value pair.

17 Claims, 3 Drawing Sheets

METHOD FOR REDUCING IMAGE NOISE IN THE CONTEXT OF CAPTURING AN IMAGE USING TWO DIFFERENT RADIATION SPECTRA

CROSS REFERENCE TO RELATED APPLICATIONS

This application claims priority of German application No. 10 2007 040 519.9 filed Aug. 28, 2007, which is incorporated by reference herein in its entirety.

FIELD OF THE INVENTION

The invention relates to a method for reducing image noise in the context of capturing at least one radiation-based image of a region of interest using two different radiation spectra, in particular two different x-ray radiation spectra.

BACKGROUND OF THE INVENTION

In so-called dual-spectrum projection radiography or dual-energy projection imaging, often abbreviated to DE imaging, an examination subject, e.g. a patient, is captured using two different x-ray spectra in order thereby to generate two projection images (raw images) of the region of interest.

By suitably combining the two raw images, two radiologically different materials such as soft tissue and bone can thus be differentiated.

Within the framework of a widely used more qualitative method of dual-energy projection imaging, only grayscale images are produced, while in the case of quantitative dual-energy imaging, physical quantities are reconstructed, i.e. reconstruction values such as material thicknesses (in cm) or areal mass densities (in $g/cm^2$), hereinafter also referred to as mass densities for short, are determined from the raw image data.

A known disadvantage of DE imaging is the marked increase in image noise compared to the raw images. For an exact quantitative reconstruction in terms of determining reconstruction values, a mathematically generally ill-conditioned system of nonlinear equations must be solved. However, this is associated with an increase in image noise.

Therefore, various noise filtering methods are already being used at present. However, these are either not based on the physically correct nonlinear model or merely constitute image post-processing in which negative correlations between separated material images are skillfully utilized for the purpose of noise reduction. Such methods are known e.g. from the articles "Quantitative evaluation of noise reduction strategies in dual-energy imaging" by R. J. Warp and J. T. Dobbins from Med. Phys. 30 (2), February 2003, and "An Algorithm for noise suppression in Dual Energy CT Material Density Images" by W. A. Kalender, E. Klotz and L. Kostaridou from IEEE Trans. Med Imaging, Vol. 7, No. 3, September 1988, 218-224, and also "A correlated noise reduction algorithm for dual-energy digital subtraction angiography" by C. H. McCollough, M. S. VanLysel, W. W. Peppler and C. A. Mistretta from Med. Phys. 16 (6), November/December 1989, 873-880.

These noise filterings and/or methods for reducing image noise are therefore non-optimal in terms of basic approach.

SUMMARY OF THE INVENTION

The object of the invention is therefore to specify a method for reducing image noise in the context of capturing at least one radiation-based image of a region of interest using two different radiation spectra, in particular using two different x-ray radiation spectra, said method constituting an improvement in this respect.

To achieve this object, a method of this kind is provided, comprising the following steps:
- capturing raw images of the region of interest using the two different radiation spectra with in each case mutually paired measured values and
- to separate different materials in the region of interest, applying to the captured raw images at least one inversion operator with integrated noise filtering, said operator describing a transition from a measured value pair to an assigned reconstruction value pair.

When performing dual-spectrum projection radiography or dual-energy projection imaging using two different x-ray spectra or radiation spectra, two projection images are therefore first produced as raw images. These raw images show the same region of interest, so that the measured values assigned to identical pixels of the image recordings can be assigned to one another as pairs.

In order now to achieve separation of two radiologically different materials such as soft tissue and bone in the region of interest or rather in the image recordings, an inversion operator is applied to these captured raw images which describes the transition from such a measured value pair for identical pixels of the raw images to an assigned reconstruction value pair, i.e. to a pair of physical quantities to be reconstructed such as a material thickness or a mass density, etc.

According to the invention, this inversion operator, which is therefore used to determine the reconstruction values, has integral noise filtering, i.e. the filtering is incorporated in the operator or linked to an inversion operator with which the reconstruction values can be determined.

For simplification, measured value pairs or reconstruction value pairs will be discussed here. However, it is likewise conceivable to capture other projection images using different energies again, for which measured values can in turn be assigned to one another for identical pixels. In this case these are no longer measured value pairs, but more generally measured value tuples, a corresponding inversion operator in this case describing the transition of such a measured value tuple to a reconstruction value tuple. Image noise reduction for such multi-energy projection images is of course also covered by the invention even if, for simplification, the following description always refers to the case of two energies or rather two different spectra for the recording.

Obviously, the raw images do not need to be captured immediately prior to applying the inversion operator with integral noise filtering, but can be captured in advance or be present as recordings which are subsequently processed in the inventive manner in order to finally obtain the correct noise-filtered image.

The measured values, hereinafter referred to as $p_1$ and $p_2$, which were captured using the different x-ray tube voltages result from the quotient of the measured intensities before and after an object to be captured in the region of interest in the same detector pixel by the formulas $$p_1 = -\ln(I_1/I_{10}),$$

$$p_2 = -\ln(I_2/I_{20}),$$

where $I_i$ are the attenuated intensities and $I_{i0}$ the unattenuated intensities.

The logarithmized measured values will hereinafter be referred to simply as measured values.

In order to get from a measured value pair to an associated reconstruction value pair, an inversion operator describing this transition can now be specified.

According to the invention, the noise filtering can be incorporated in the inversion operator by determining the latter for smoothed raw image measured value pairs captured using the different radiation spectra. The reason behind this procedure is that the inversion operator is essentially determined by material properties and the x-ray spectra. It is therefore not useful or in a certain sense excessive to incorrectly interpret random measured value errors due e.g. only to quantum noise as variations in the material properties in the region of interest by modifying the inversion operator itself on the basis of these measured value errors. The invention therefore assumes that the inversion operator is not determined directly for the captured measured value pairs, but for smoothed measured value pairs of the raw images. The two raw images for the lower or higher voltage at the x-ray radiation generator are therefore smoothed and this smoothed data used for determining the inversion operators.

In particular, the measured value pairs of the raw images can be adaptively smoothed. This involves edge-eliminating smoothing. Other smoothing methods not mentioned here can be additionally used or different useful smoothing methods can be employed for smoothing the raw images.

An inversion operator can then be determined for each identical pixel pair of the smoothed raw images using an assigned smoothed measured value pair. Therefore, for each measured value pair constituted by the measured values for identical pixels of the raw images, an inversion operator is determined which determines the transition between the measured values and desired reconstruction values. As the inversion operator is specified for the smoothed measured value pairs, it already contains noise filtering incorporated in the operator itself.

At least one inversion operator determined for smoothed raw images captured using the two different radiation spectra can then be applied to a corresponding actual measured value pair of the unsmoothed raw images to determine a reconstruction value pair.

The inversion operator which was determined for smoothed raw data is therefore now applied in the form of operator smoothing to the original raw image data prior to smoothing to determine the reconstruction value pairs, i.e., for example, a material thickness and the like. In this way, noise-reduced reconstruction values are obtained.

The method can be executed in a largely automated manner using a program means e.g. on a control device of a corresponding x-ray device.

In particular, at least one inversion matrix can be determined as at least one inversion operator, in particular a 2×2 matrix for each, if necessary smoothed, measured value pair of the raw images. Determining a 2×2 matrix for describing the transition from measured values to reconstruction values is advisable if, as is generally the case, pairs of measured values are present, i.e. projection images were captured using two different spectra, i.e. in the context of dual-energy imaging.

A pair of measured values captured using the two different radiation spectra can be assigned a pair of mass densities and/or material thicknesses as at least one reconstruction value pair, the material thicknesses being generally specified in cm and the mass densities in $g/cm^2$. Additional or different reconstruction values or rather pairs can of course likewise be determined from the measured values.

Within the scope of the method according to the invention, a pair of smoothed measured values captured using the different radiation spectra can be assigned a theoretical value pair. This means that each pair of measured values $(p_1, p_2)$ genuinely measured is assigned a theoretical value pair $(M_1(\overline{b}), M_2(\overline{b}))$ with which the measured value pair is to be identified, the vector $\overline{b} = (b_1, b_2)$ denoting a pair of reconstruction values $b_1$ and $b_2$.

For the theoretical values $M_1(\overline{b})$ and $M_2(\overline{b})$ which describe the logarithmic primary attenuation, we get $$M_1(b_1, b_2) = -\ln\left(\int_0^{eU_1} e^{-\alpha_1(E)b_1 - \alpha_2(E)b_2} W_1(E)\,dE\right)$$

$$M_2(b_1, b_2) = -\ln\left(\int_0^{eU_2} e^{-\alpha_1(E)b_1 - \alpha_2(E)b_2} W_2(E)\,dE\right)$$

where $W_1(E)$ and $W_2(E)$ denote the respective capturing spectra, and $\alpha_1(E) = (\mu_1/\rho_1)(E)$ and $\alpha_2(E) = (\mu_2/\rho_2)(E)$ specify the mass attenuation coefficients, the attenuations being specified by $\mu_i$ and the densities by $\rho_i$. Integration is over the interval from 0 to the respective tube voltage multiplied by the elementary charge.

The effective spectra $W_1(E)$ and $W_2(E)$, which incorporate the emission spectra of the x-ray tube at the two different voltages as well as spectral filters and an energy-dependent detector responsivity, are known and normalized such that the integral comes out to 1. Basically, the assignment between a measured value pair and a reconstruction value pair can be calculated in advance and stored in tabular form. For a discretization of 1000 values for the logarithmized measured values, the table then comprises $2*10^6$ entries.

However, for the method according to the invention a different procedure based on linearization is applied.

According to the invention, each reconstruction value pair is assigned a pair of discrete energies for this purpose.

This means that initially (equivalent) discrete energies $$E_1 = E_1(b_1, b_2)$$

and $$E_2 = E_2(b_1, b_2)$$

are specified.

For each theoretical value pair, a coefficient matrix with coefficients dependent on the discrete energies is then determined which specifies the transition from a reconstruction value pair to the assigned theoretical value pair. Linear relations $$M_1(b_1, b_2) = \alpha_1(E_1)b_1 + \alpha_2(E_1)b_2$$

and $$M_2(b_1, b_2) = \alpha_1(E_2)b_1 + \alpha_2(E_2)b_2$$

can therefore be specified which represent the relationship between the individual components $M_1$ and $M_2$ of the theoretical value pairs and the corresponding components $b_1$ and $b_2$ of the reconstruction value pairs. The coefficients of these linear relations, i.e. the coefficients $\alpha_i(E_k)$, form a coefficient matrix whose entries each represent mass attenuation coefficients $\alpha_i$. This matrix will hereinafter be termed matrix A. In order to show the dependence of matrix A on the reconstruction value pairs, it may be provided with a corresponding subscript ($\underline{b}$), $$A_{(\underline{b})} = \begin{pmatrix} \alpha_1(E_1) & \alpha_2(E_1) \\ \alpha_1(E_2) & \alpha_2(E_2) \end{pmatrix},$$

the measured value pairs being given by $$\underline{p} = M(\underline{b}) = A_{(\underline{b})}\underline{b}$$

According to the invention, the coefficient matrix for generating an inversion operator and subsequently determining a reconstruction value pair assigned to an actual value pair as a function of an associated smoothed measured value pair can then be inverted. The inversion, i.e. the back-calculation from a pair of measured values $p=(p_1, p_2)$ to the associated pair of reconstruction values $b=(\overline{b}_1, b_2)$, e.g. of material thicknesses, can be performed by inverting matrix A.

According to the invention, it is therefore not absolutely necessary, in contrast to the existing method, to specify a table in which each measured value pair is assigned a pair of reconstruction values, but the table can also be set up such that each measured value pair is initially assigned the associated inversion matrix or rather its four coefficients. During inversion of the matrix, its dependence on the reconstruction value pair changes to a dependence on the measured value pair $\underline{p}$ so that $$\underline{b} = A_{(\underline{p})}^{-1}\underline{p}$$

where $A_{(\underline{p})}^{-1}$ denotes the inverted matrix dependent on the measured value pair $\underline{p}$, noise filtering being incorporated in said inverted matrix e.g. as described below.

If the nonlinear relationship described above is disregarded, e.g. using a constant inversion matrix, considerable errors in the order of one to two centimeters can arise when determining a material thickness, for example. This is inventively counteracted by performing a nonlinear inversion using a measured-value-dependent matrix as described.

As it is assumed that the measured values, i.e. the raw data, are affected by noise, another error, namely the noise, is additively combined with the exact measured value pair. Without noise filtering being incorporated in the matrix, the raw data noise would be transferred to the reconstruction values calculated with the aid of the inversion matrix and even amplified if the matrix condition is poor. This would be the case even if the matrix were measured-value-independent, but even more so for a measured-value-dependent inversion matrix or a measured-value-dependent inversion operator. In such a case, the noise is further modified by the inversion matrix itself, resulting in noise amplification. Simulations show that, e.g. in the case of a material combination of twenty centimeters water and a few centimeters bone, the pixel noise increases by thirty percent if the inversion is performed measured-value-dependently, i.e. in direct dependence on the raw value pair captured.

The situation is different in the scenario according to the invention, i.e. if the operator is determined as a function of the associated smoothed measured value pair, not for the actual measured value pair. The noise filtering can of course in principle also be incorporated in the inversion operator in some other way.

Of paramount importance, however, is the inventive concept of no longer changing the inversion matrix and/or the inversion operator on the basis of the measured value errors, i.e. determining it for already smoothed raw images. A reconstruction value pair can then be determined with a significantly reduced error by applying said smoothed operator to the unsmoothed raw image data.

This procedure can be described by the formula $$\underline{b}^{\sim} = A_{(S\underline{p})}^{-1}\underline{p}$$

in which the subscript (Sp) of the inverse matrix $A^{-1}$ indicates that the matrix pertains to adaptively pre-smoothed raw data. The adaptive smoothing operator is denoted by the symbol S. The resulting modified reconstruction value pair is denoted by $b^{\sim}$.

According to the invention it is therefore proposed to tabulate for each measured value pair the four coefficients of a 2×2 matrix A or the associated inverses, instead of assigning each measured value pair only the associated pair of reconstruction values. For multi-energy imaging, correspondingly larger matrices must be tabulated. By means of the proposed form of tabulation, greater flexibility in respect of the usability of noise filtering methods is achieved.

By means of the proposed operator smoothing, the noise as the standard deviation of the pixel noise can be reduced by typically about twenty-five percent, thereby improving the signal-to-noise ratio accordingly.

The advantage of this is that the patient dose, i.e. the patient's radiation load, can be significantly reduced, typically to $0.75^2=56\%$ of the existing value, with no accompanying deterioration in image quality.

The method can self-evidently also be applied to series of projection images which are further processed for image reconstruction in computed tomography.

In addition, after application of the inversion operator, at least one further noise filtering can be performed. The inventive filtering method which precedes the actual material separation in that the filtering is already incorporated in the operator by determining the latter for smoothed data, can therefore be advantageously combined with different post-processing noise filtering methods and algorithms in order to thus obtain a further improvement in the (quality of the reconstructed) data.

In addition, at least one calibration and/or correction method is expediently applied to the captured raw images to eliminate systematic inaccuracies prior to smoothing and/or scatter is eliminated from the raw images. For optimum results it is accordingly to be assumed that the measured data no longer contains systematic inaccuracies apart from noise and that the scatter has also been eliminated.

The method can be carried out by a computing device and/or automatically and/or in an operator-assisted manner, in particular using at least one program means.

There can therefore be provided e.g. an x-ray device or more specifically a device for producing radiation-based recordings which has a control device in the form of a computing device which in turn has access to at least one program means or on which program means are stored with the aid of which the inventive determination of reconstruction values on the basis of operator smoothing is carried out, automatically if required, after capturing of the raw images. Reconstruction value determination can be fully automated, i.e. such that, for example, an operator merely initiates capturing of the measured data, whereupon the rest of the image reconstruction process is executed completely automatically. However, it is also conceivable for the inventive noise filtering to be initiated separately by an operator after capturing of the raw image data or rather carried out allowing for further operator inputs, e.g. in respect of a particular smoothing method to be selected or of a selection of suitable post-processing noise filtering algorithms.

In the inventive method with operator smoothing, for each measured value pair, four real numbers must be tabulated, namely the four coefficients of the inversion matrix. This means that the table would contain $4*10^6$ entries when the measured values are discretized into a thousand values in each case. In addition, it is necessary that, at least temporarily, not only the raw image data but also the smoothed raw image data can be accessed by the computing device.

If a specific measured value pair does not fall in the discretization grid or not exactly into said grid, according to the invention the four inversion matrix coefficients can be obtained from the table e.g. in a bilinear manner by interpolation methods.

In the case of bilinear interpolation, for example, this means for each pixel an overhead of approximately twenty additions and multiplications, namely 4*4 operations for the bilinear interpolations and additionally four operations for the matrix vector multiplication. The additional determination of the bilinear interpolation weights comprises approximately six multiplications, resulting in an altogether acceptable memory requirement or computational overhead.

BRIEF DESCRIPTION OF THE DRAWINGS

Further advantages, features and details of the invention will emerge from the following exemplary embodiments and the accompanying drawings, in which.

DETAILED DESCRIPTION OF THE INVENTION

Figure 1:
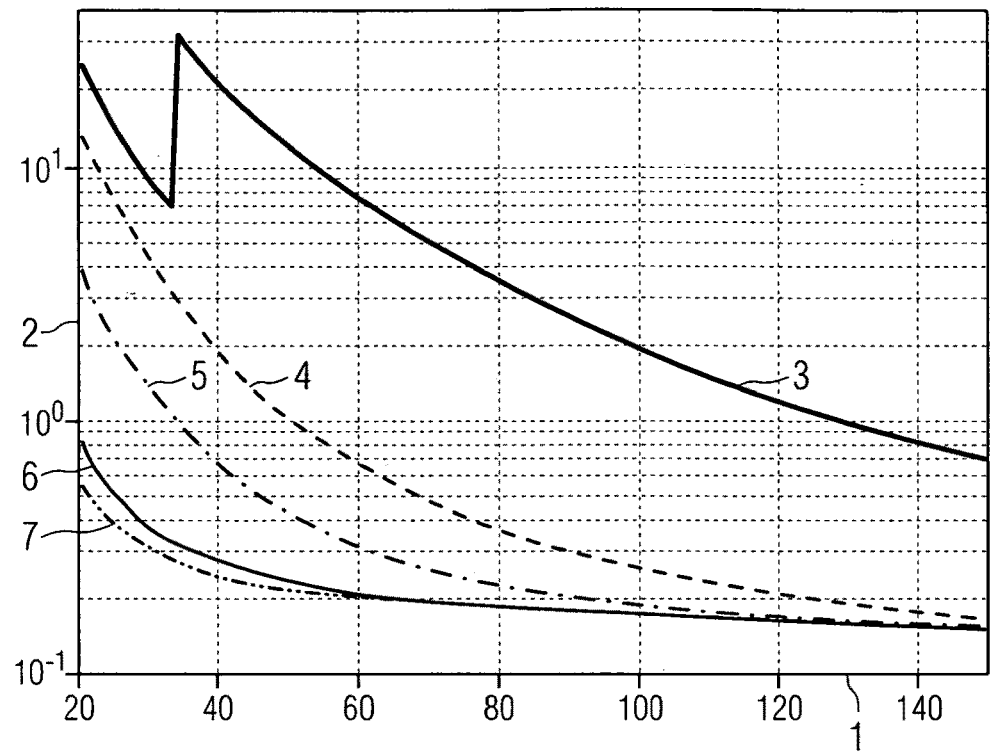
FIG. 1 shows energy-dependent mass attenuation coefficients for various materials.

FIG. 1 plots energy-dependent mass attenuation coefficients $(\mu/\rho)(E)$ in $cm^2/g$ for various materials, $\mu$ denoting the attenuation, $\rho$ the density and E the energy. On the x-axis 1 the values of the photon energy are given in keV (kiloelectron volts), while the associated mass attenuation coefficients in $$\frac{cm^2}{g}$$

are plotted on the y-axis 2 in logarithmic form. Curve 3 represents the energy-dependent characteristic of the mass attenuation coefficient for iodine, curve 4 that for calcium, curve 5 the characteristic for bony tissue, and curves 6 and 7 the energy-dependent mass attenuation coefficients for water and fatty tissue.

According to curve 3, iodine exhibits the highest mass attenuation coefficient over the entire energy range, while that for fatty tissue according to curve 7 is the lowest. Most closely comparable to the progression of curve 7 for fatty tissue is the progression of the mass attenuation coefficient as a function of energy for water according to curve 6.

At lower energies, bony tissue and calcium exhibit much higher mass attenuation coefficients compared to curves 6 and 7. At higher energies, curve 5 increasingly approximates to curves 6 and 7 for water and fatty tissue respectively. On the other hand, according to curve 4 calcium also has a noticeably greater mass attenuation coefficient in the region of 140 keV.

Figure 2:
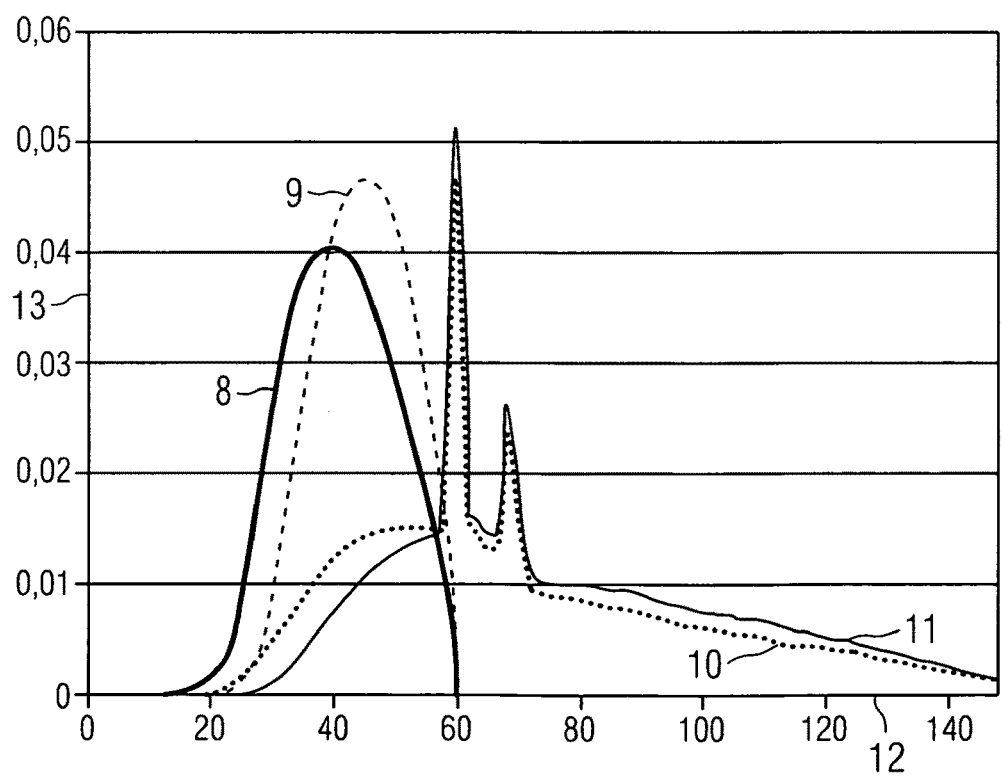
FIG. 2 shows typical dual-energy spectra for dual-energy projection imaging.

FIG. 2 shows four typical dual-energy spectra according to curves 8, 9, 10 and 11. These spectra are normalized spectra for various voltages and pre-filterings, the quantum energy in keV being plotted on the x-axis 12, while the normalized intensity is plotted on the y-axis 13.

Curve 8 represents the energy-dependent intensity for a voltage of 60 kV with pre-filtering by 0.1 mm copper, while curve 9 is based on pre-filtering by 0.3 mm copper at the same voltage.

Curves 10 and 11 are each assigned to voltages of 150 kV, curve 10 representing the spectrum for pre-filtering with 0.1 mm copper, and curve 11 that for pre-filtering with 0.3 mm copper.

Whereas, for the lower voltages, curves 8 and 9 correspondingly show a clear peak at lower quantum energies and the respective intensity value has already fallen to 0 at 60 keV, at the higher voltages the spectra are broader and instead exhibit two smaller peaks. The different pre-filterings result in further deviations in the curve shapes, e.g. at low voltage in a shift of the peak into the higher-energy region. As the respective spectra should overlap as little as possible at lower or higher voltage, it is advisable e.g. to pre-filter at 60 kV with only 0.1 mm copper, but at 150 kV with 0.3 mm copper.

Figure 3:
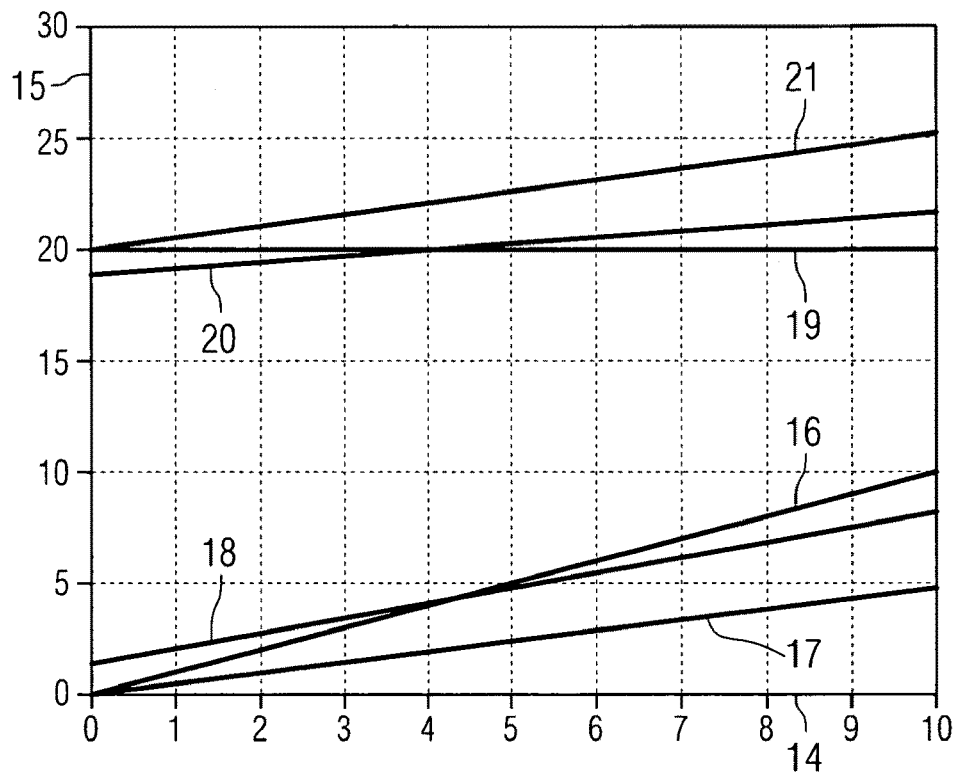
FIGS. 3 and 4 show illustrations of the quantitative inaccuracy when using a constant inversion matrix compared to exact nonlinear inversion and FIGS. 5 and 6 show simulated results of an inventive method for reducing image noise.
Figure 4:
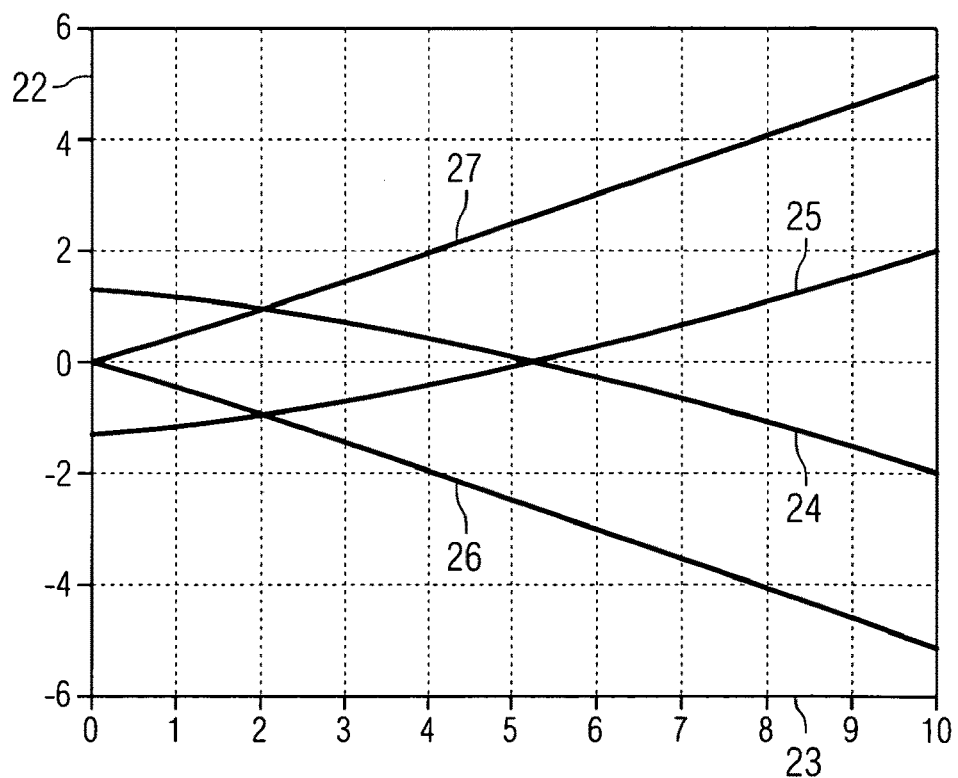

FIGS. 3 and 4 show illustrations of the quantitative inaccuracy when using a constant inversion matrix as compared to a measured-value-dependent matrix.

Plotted on the x-axis 14 in FIG. 3 is an actual bone thickness in grams per $cm^2$ ($g/cm^2$), while the reconstructed thickness is shown on the y-axis 15, likewise in grams per $cm^2$. The exact, nonlinear inversion corresponds, for bony tissue, to curve 16. Curve 17 represents the clearly deviating characteristic when using a constant matrix, i.e. an approximation instead of the exact matrix, for 20 cm water and 0 cm bony tissue, the curve 18 the results for a constant matrix for 20 cm water and 5 cm bony tissue. The exact ratios corresponding to nonlinear inversion are given by curve 19 for water, the approximations for 20 cm water with 5 cm bony tissue by curve 20, and for 20 cm water with 0 cm bony tissue by curve 21.

The associated reconstruction errors in grams per $cm^2$ ($g/cm^2$) are plotted on the y-axis 22 of FIG. 4 against the true bone thickness in grams per $cm^2$ on the x-axis 23.

Curves 24 for bone and 25 for water represent the errors for 20 cm water and 5 cm bone respectively, while curves 26 and 27 for bone and water respectively show the reconstruction error for 20 cm water and 0 cm bony tissue.

These curves 24-27 indicate that the reconstruction errors may well be in the order of several grams per $cm^2$. Even in the case of 20 cm water and 5 cm bony tissue according to curves 24 and 25, deviations of almost 2 grams per $cm^2$ are possible at high actual bone densities. Even at very low actual bone densities, the deviations are more than one gram per $cm^2$. In the case of 20 cm water and 0 cm bone, the error increases to some $\pm 5$ $g/cm^2$ for an actual bone thickness of 10 $g/cm^2$.

Accordingly, for meaningful quantitative imaging it is unacceptable to disregard the measured value dependence of the matrix.

Figure 5:
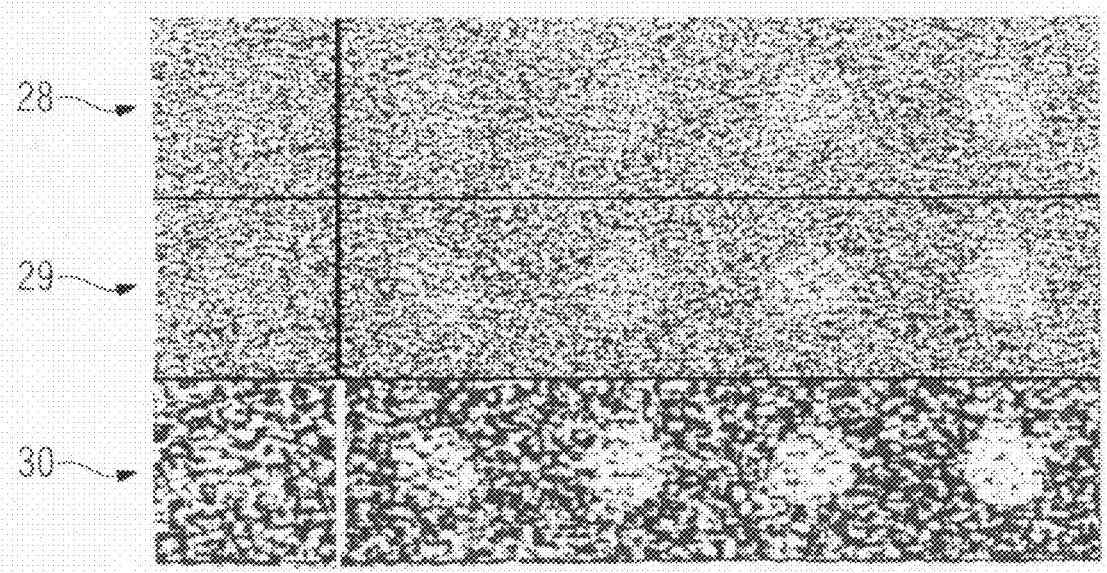
Figure 6:
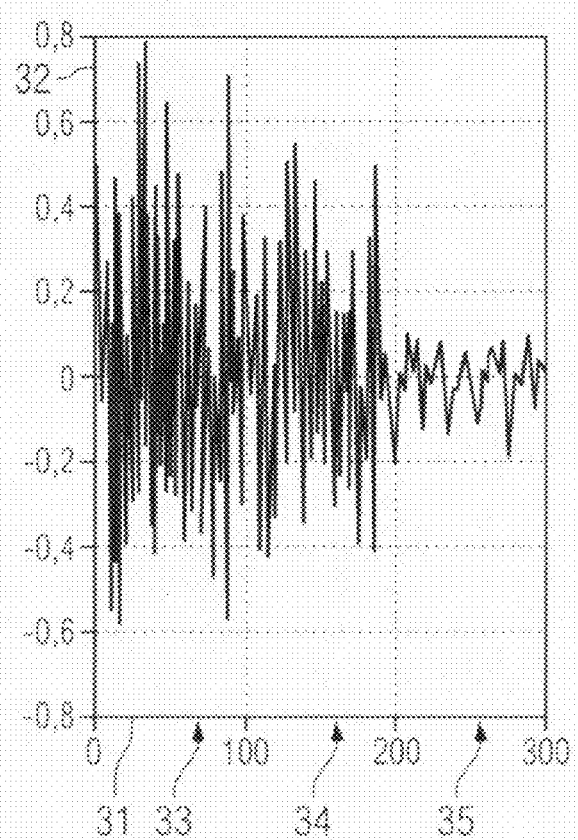

Lastly, FIGS. 5 and 6 show simulated results of an inventive method for image noise reduction. The illustration relates to a simulation object in the form of a homogeneous layer of water with a thickness of 20 cm above which are disposed circular disks of bone with diameters of 20 pixels each whose mass densities vary between 50 and 250 $mg/cm^2$ in increments of 50 $mg/cm^2$. The radiation source used is an x-ray tube with a tungsten anode and internal filtering corresponding to 2.5 mm aluminum. The detector is a flat-panel detector with cesium iodide with a density of 100 mg/cm² as scintillator material. The radiation spectra employed are spectra with a voltage of 70 kV with pre-filtering of 0.1 mm copper and with a voltage of 150 kV with pre-filtering of 0.3 mm copper respectively. Taken as the basis for the noise of the measured signal at the detector is a noise equivalent quantum number of 1000, the relative standard deviation of the noise for each detector pixel corresponding to $$\frac{1}{\sqrt{1000}} \approx 3.16\%.$$

The first row 28 shows the unfiltered bone image according to the additionally specified equation (1) $A_{(p)}^{-1}(\underline{p})$.

The second row 29 shows the reconstruction result of the inventive operator smoothing method according to equation (2) $A_{(Sp)}^{-1}(\underline{p})$. This allows improved object recognition. Accordingly the result shows fewer errors.

Row 30 finally shows the reconstruction result for combining the operator smoothing method with subsequent image smoothing according to the formula (3) $SA_{(Sp)}^{-1}(\underline{p})$.

In FIG. 6, pixel counts are plotted on the horizontal axis 31, while the error in grams per cm² (g/cm²) with noise filtering according to matrix formulas (1), (2) and (3) is plotted on the vertical axis 32.

It can be seen from this that for exact inversion without filtering according to column 33 (for matrix formula (1)) even larger errors occur, which are already significantly reduced in the case of the operator smoothing method of the invention according to column 34 (formula (2)). A further error reduction is achieved by combination with subsequent image filtering using a 5×5 mask according to column 35 (formula (3)). When the operator smoothing method is combined with subsequent image smoothing, the error can be continuously kept below 0.2 g/cm². Even when simply using the operator smoothing method according to column 34 without subsequent smoothing, errors of more than 0.4 g/cm² rarely occur.

The inventive noise filtering which is incorporated in an inversion operator therefore provides a significant improvement in quantitative imaging in the context of dual-spectrum projection imaging.

The invention claimed is:

1. A method for reducing an image noise, comprising:
   capturing raw images of a region of interest of a patient using two different radiation spectra with mutually a measured value pair;
   smoothing the measured value pair of the captured raw images by performing a noise filtering;
   determining an inversion operator based on the smoothed measured value pair; and
   applying the inversion operator with the integrated noise filtering to the captured raw images for a transition from the measured value pair to an assigned reconstruction value pair to separate different materials in the region of interest.

2. The method as claimed in claim 1, wherein the measured value pair is adaptively smoothed.

3. The method as claimed in claim 1, wherein the captured raw images are smoothed by the smoothed measured value pair.

4. The method as claimed in claim 3, wherein the inversion operator is determined using the smoothed measured value pair assigned to each identical pixel pair of the smoothed raw images.

5. The method as claimed in claim 4, wherein the inversion operator determined for the smoothed raw images is applied to a corresponding measured value pair of the captured raw images to determine the reconstruction value pair.

6. The method as claimed in claim 1, wherein a theoretical value pair is assigned to the smoothed measured value pair.

7. The method as claimed in claim 6, wherein a pair of discrete energies is assigned to the reconstruction value pair.

8. The method as claimed in claim 7, wherein a coefficient matrix with coefficients depending on the discrete energies is determined for a transition from the reconstruction value pair to the assigned theoretical value pair.

9. The method as claimed in claim 8, wherein the coefficient matrix is inverted for generating the inversion operator and determining the reconstruction value pair assigned to the measured value pair as a function of the smoothed measured value pair.

10. The method as claimed in claim 1, wherein the inversion operator is an inversion matrix.

11. The method as claimed in claim 10, wherein the inversion matrix is a 2×2 matrix.

12. The method as claimed in claim 1, wherein a pair of mass densities or material thicknesses is assigned to the measured value pair as the reconstruction value pair.

13. The method as claimed in claim 1, wherein an additional noise filtering is performed after applying the inversion operator.

14. The method as claimed in claim 1, wherein a calibration or a correction is applied to the captured raw images prior to smoothing the captured raw images to eliminate systematic inaccuracies or scatters.

15. The method as claimed in claim 1, wherein the method is carried out by a computing device automatically or assisted by an operator.

16. The method as claimed in claim 1, wherein the two different radiation spectra is two different x-ray radiation spectra.

17. The method as claimed in claim 1, wherein the different materials comprise soft tissues and bone of the patient.

* * * * *